United States Patent
Fry et al.

(10) Patent No.: US 6,346,267 B1
(45) Date of Patent: Feb. 12, 2002

(54) COMPOSITION AND METHOD FOR TREATMENT OF SYMPTOMS ASSOCIATED WITH INSUFFICIENT ESTROGEN PRODUCTION

(75) Inventors: Kathleen K. Fry, Scottsdale, AZ (US); Claudia J. Wingo, College Park, MD (US)

(73) Assignee: Wakunaga of America Co., Ltd., Mission Viejo, CA (US)

( * ) Notice: Subject to any disclaimer, the term of this patent is extended or adjusted under 35 U.S.C. 154(b) by 0 days.

(21) Appl. No.: 09/612,299

(22) Filed: Jul. 7, 2000

(51) Int. Cl.$^7$ .............................. A61K 9/20; A61K 9/48
(52) U.S. Cl. ...................... 424/451; 424/455; 424/456; 424/464; 424/489
(58) Field of Search ................................ 424/451, 456, 424/489, 455, 464

(56) References Cited

U.S. PATENT DOCUMENTS 5,565,199 A * 10/1996 Page et al. ................ 424/195.1
5,569,459 A * 10/1996 Shlyankevich ........... 424/195.1
6,200,594 B1 * 3/2001 Ernest et al. ............... 424/439

* cited by examiner

Primary Examiner—James M. Spear
(74) Attorney, Agent, or Firm—Oblon, Spivak, McClelland, Maier & Neustadt, P.C.

(57) ABSTRACT

A composition and method are provided for the treatment of symptoms associated with reduced estrogen production, such as occurs in perimenopausal and menopausal women, wherein the composition contains at least one phytoestrogen containing food, herb or extract thereof, and at least four herbs or extracts which are effective at treating conventional menopausal symptoms.

20 Claims, No Drawings

COMPOSITION AND METHOD FOR TREATMENT OF SYMPTOMS ASSOCIATED WITH INSUFFICIENT ESTROGEN PRODUCTION

BACKGROUND OF THE INVENTION

1. Field of Invention

The present invention relates to a method and composition for prevention, mitigation and treatment of symptoms caused by insufficient estrogenic hormonal levels, such as occurs during menopause, wherein the method uses a composition containing (1) herbs having substantial recognized activity as phytoestrogens such as soy isoflavones, black cohosh, and wild yam and (2) other herbs which have been traditionally used for alleviating menopausal and related symptoms, such as sage, chastetree berry, vervain, astragalus and motherwort.

2. Background Art

Menopause is a cessation of menses, the end of menstrual cycles. The years just prior to menopause are known as perimenopause. As one ages, follicles become fewer in number and don't develop fully. For example, a follicle from a woman who is 40 is not as strong and healthy as a follicle from a woman who is in her twenties. Reduced follicle development leads to less estrogen being produced. The pituitary detects that low estrogen level and tries to stimulate the ovary to make more estrogen by releasing more follicle stimulating hormone (FSH). However, reduced follicle numbers or size will not allow for the production of any more estrogen. Thus, estrogen does not reach a peak strong enough to stimulate the luteinizing hormone (LH) surge. Without the LH surge, there is no ovulation. Without ovulation, there is no progesterone. Without progesterone, women begin to skip cycles. During this period, most women experience unpleasant symptoms, such as hot flashes, anxiety and/or depression, tiredness/fatigue, and vaginal dryness, all at least in part due to the hormonal imbalance. Such symptoms last for more than one year in 80% of women and for up to five years in one in three women. Perimenopause, the transition time into menopause, is officially diagnosed when a woman is over 40 and experiencing such symptoms.

Many trials have been conducted to ameliorate these menopause symptoms by administrating phytoestrogens derived from herbs. Especially, soybean isoflavones have been studied extensively and have demonstrated a number of health benefits, including relief of menopausal symptoms (JP-10-114653,JP7-506822). Soybean isoflavones have been marketed and acquired a feasible reputation as dietary supplements to alleviate menopause and related symptoms and reduce the risk of osteoporosis and breast cancer.

Other herbs, such as black cohosh, wild yam, chastetree berry, sage, vervain and astragalus have also been used historically to ameliorate menopause and related symptoms. Many supplements containing these herbs have been marketed for quite a long time. Most of these products contain either single herbs or two or more herbs combined, or herbs combined with minerals and vitamin D, which enhance the osteogenesis activity.

Although these products have been used as menopause remedies for a long time, their effectiveness has not really been satisfactory to the majority of women.

Previously, the present inventors have also used a formula consisting of soy, red clover, black cohosh and wild yam (Table 1, formula #1) in their clinical practices. Unfortunately, the efficacy of this formula against menopause symptoms, such as hot flash, insomnia and vaginal dryness, was not satisfactory. Furthermore, many patients who received this formula complained of several complications such as tiredness, absent-mindedness, and lack of energy, after taking this remedy.

SUMMARY OF THE INVENTION

Accordingly, one object of the present invention is to provide a composition useful for treatment of symptoms caused by insufficient estrogen production, particularly those associated with menopause and perimenopause, without the side-effects produced by previous treatments.

A further object of the present invention is to provide a method for the treatment of symptoms associated with insufficient estrogen production using a herbal formula without the side-effects of previous remedies.

These and other objects of the present invention have been satisfied by the discovery of a composition containing (1) at least one herb containing phytoestrogens and (2) at least four members selected from the group consisting of sage, vervain, astragalus, motherwort and chastetree berry, that provides relief from the symptoms associated with insufficient estrogen production, particularly during perimenopause and menopause, without the difficult side-effects of tiredness, absentmindedness and lack of energy seen in previous formulations and providing alleviation of common menopause symptoms such as hot flash, insomnia and vaginal dryness.

DETAILED DESCRIPTION OF THE INVENTION

The present invention relates to a composition comprising two types of herbs: (1) herbs containing phytoestrogens and (2) traditional herbs which ameliorate women's discomfort, for prevention, alleviation and treatment of various unpleasant symptoms due to the decreased estrogenic hormones around menopause. The term "phytoestrogens" refers to natural plant chemicals that mimic estrogen and have estrogenic activities. Representative examples of herbs containing phytoestrogens are soy, black cohosh, and wild yam. Preferably, the composition comprises two or more herbs selected from those containing phytoestrogens, more preferably three or more herbs containing phytoestrogens, most preferably all three of the following phytoestrogen containing herbs: soy isoflavone, wild yam and black cohosh. The phytoestrogen levels can be further improved by consumption of various foods high in isoflavones or phytoestrogens, including but not limited to, broccoli, carrots, cauliflower, Brussels sprouts, snow peas, flaxseed oil, lentils, beans, chick peas, soybean products, cherries, apples, peas, stone fruits, linseed, sunflower seeds, fennel, vegetable oils including olive oil, and alfalfa.

The composition also contains a plurality of herbs used for the treatment of symptoms arising from decreased estrogenic hormone levels. Representative examples of traditional herbs which have been used for this type of women's discomfort are sage, motherwort, astragalus, vervain, chastetree berry, St Johns wort, panax ginseng, dong quai, licorice, damiana, raspberry leaves, fennel, ginseng and gotucola, with sage, motherwort, astragalus, vervain and chastetree berry being preferred. The present composition preferably contains at least four of the above named herbs, more preferably five of the above named herbs, most preferably, the herbs sage, motherwort, astragalus, vervain and chastetree berry.

Another notable phytoestrogen containing herb is red clover. However, the present inventors have found that use of red clover has an adverse effect on menopausal symptoms when used in conjunction with other phytoestrogens. This type of formulation is summarized in Table 1, formula #1. As noted above, women administered that formula complained of tiredness, absentmindedness and a lack of energy, as well as hot flashes, insomnia and vaginal dryness.

This invention is based on the new findings that by adding wild yam, sage, vervain, astragalus and motherwort instead of red clover to the previous formula (Table 1, formula #2), tiredness, absentmindedness and lack of energy, which have been observed in formula #1, were drastically diminished. Furthermore, other common menopause symptoms, such as hot flush, insomnia, and vaginal dryness, were also alleviated in the majority of the patients.

The ingredients comprising the present invention are either extracts which contain higher dosages of active ingredients or powders of a corresponding part of the herb. In the former case, admixture of herbal extracts can be processed into tablet, capsules, soft gelatin capsules, powders, granules and liquid products in combination with appropriate pharmaceutical excipients or food ingredients. In the latter case, herbs can be provided as tea-packs for decoction after being dried, cut and packaged. Further, a fine powder of herbs can be processed into suitable form as a drug or as a dietary supplement as mentioned above.

Generally, the daily dosage of herbs containing phytoestrogens is about 0.1 to about 10,000 mg, preferably, about 1 to about 500 mg as an extract. More preferably, about 1 to about 300 mg soy isoflavones, about 1 to about 300 mg black cohosh and about 1 to about 300 mg wild yam extract are used in the composition. Of course, when extracts are used, the amount of extract will be dependent on the concentration of the extract. While there is no limitation of the concentration of extract useful for the present invention, it is noted that extract concentrations of 1:1–100:1 are preferred, with concentrations of 2:1–50:1 being more preferred. Any extract concentration can be used, and should be used in an amount to provide an equivalent level of the herbal activity to that achieved using the the entire herb in the ranges recited herein. This amount is referred to herein as the "equivalent extract dosage".

The daily dosage of other herbs which have been used for women's health, such as vervain, chastetree berry, astragalus, motherwort and sage, is about 0.1 to about 10,000 mg, preferably about 1 to about 300 mg. In a more preferred embodiment, the daily dosage is about 1 to about 300 mg sage, about 1 to about 300 mg chastetree berry, about 1 to about 300 mg Vervain, about 1 to about 300 mg astragalus and about 1 to about 300 mg motherwort.

According to the present invention, a composition is provided comprising about 1 to about 500 mg soy isoflavones, about 1 to about 500 mg black cohosh extract, about 1 to about 500 mg sage extract, about 1 to about 500 mg chastetree berry extract, about 1 to about 500 mg vervain extract, about 1 to about 500 mg astragalus extract and about 1 to about 500 mg motherwort extract in admixture to prevent and/or alleviate various symptoms around the to menopause period due to decreased estrogenic hormones. In a most preferred embodiment, the amounts of components of the present composition are about 30 to about 70 mg soy isoflavones, about 80 to about 120 mg black cohosh extract (4:1 extract), about 40 to 120 mg wild yam, about 5 to about 75 mg sage extract (4:1 extract), about 5 to about 45 mg chastetree berry extract (4:1 extract), about 5 to about 45 mg vervain extract (4:1 extract), about 5 to about 45 mg astragalus extract (4:1 extract) and about 5 to about 45 mg motherwort extract (4:1 extract) in admixture to prevent and/or alleviate various symptoms around the menopause period due to decreased estrogenic hormones.

The composition of the present invention can be administered either in a single daily dosage or in several dosages per day, to provide a total daily dosage of from 0.1 to 10,000 mg/day, preferably from 30 to 800 mg/day. If administered in multiple dosages per day, the dosages can be equal doses or variable strength. Preferably, the composition is administered to the subject up to 4 times per day to arrive at the desired daily dosage. When administered in multiple dosages, it is preferred to administer equal dosages, primarily for the patient's convenience. If unequal dosages are used, the dosages should be adjusted to provide an approximately equal level of the composition's active ingredients in the bloodstream throughout the day, with larger dosages being provided when the time between doses is higher and smaller dosages being provided when the time between doses is shorter.

Treatment with the present composition should begin as soon as perimenopausal symptoms appear or diagnosis is made. The treatments preferably continue throughout the perimenopausal and menopausal transition, most preferably continuing even after menopause has been entered. In a preferred embodiment, treatment can be begin even before perimenopause is entered, generally starting between the ages of 35 and 40 years of age. This permits the herbal composition to help ease the transition into perimenopause and further into menopause.

While the use of herbal compositions to treat symptoms associated with menopause has been widely attempted in the past, the compositions previously used did not address all of the difficulties experienced by perimenopausal women. The present composition provides relief from the symptoms associated with reduced estrogen production, while avoiding the common side-effects of fatigue and absentmindedness associated with typical phytoestrogen based treatments.

Herbs Used in the Present Composition

Black cohosh (*Cimicifuga racemosa*)

Black cohosh, a native plant to North America and Canada, is a perennial plant with triterpene glycosides (cimicifugoside, acein, racemoside), isoflavones (formononetin), aromatic acids (isoferulic and salicylic acids), resin, tannins, fatty acids as active ingredients. Historically, it has been used as an anti-inflammatory and sedative in treating female reproductive complaints such as painful menstrual cramping, delayed periods, mastitis, ovarian pain and other menopausal symptoms.

Soy (*Glycine max.*)

Epidemiological studies in Asia have shown a much lower rate of heart disease, breast, colorectal and prostate cancer in the general population as well as fewer menopausal symptoms in Asian women. Soybeans are the richest food source of a type of "phytoestrogen" called isoflavones (genistein, daidzein and glycitin). These isoflavones bind to estrogen receptors sites acting like a mild form of estrogen, thus bringing a number of benefits to the body.

Wild yam (*Dioscorea Visa*)

The wild yam plant is native to North and Central America but can now be found in many semitropical and temperate areas throughout the world. The Medicinal part of the plant is the yellowish dried rhizome and root or tuber which contains steroidal saponins (mainly dioscin), isoquinuclidine alkaloids (dioscorin), phytoesterols (beta-sitosterol) and tannins. Steroidal saponin, mainly dioscorin, could be converted into diosgenin, a precursor of progesterone and the corticosteroids. This herb has been used as an anti-inflammatory, relieving spasmodic pain in the female reproductive organs.

Sage (*Salvia officials*)

Its name "salvia" is taken from the Latin word meaning "to cure".

Active constituents include volatile oils (thujone, 1,8-cineole, camphor, bornrol and others), diterpenes (picrosalvin, camosolocacod), triterpenes, flavonoids and phenolic acids. It has been traditionally used during menopause to help the body deal with hormonal changes as well as hot flashes and excessive perspiration, common and often distressing symptoms of menopause.

Chastetree berry (*Vitex agnus castes*)

Chastetree berry is native to the Mediterranean area and has been used for female reproductive problems. Clinical tests over the past 40 years have shown that chastetree berry exerts a hormonal action to balance estrogen and progesterone levels in the body. Its active ingredients include iridoid glycosides (agnuside, aucubin and eurostoside), pseudoindicans, flavonoids (casticin, orientin and isovitexin) and volatile oils (α-pinene, sabinene, limonene, and 1,8-cubeike).

Astragalus (*Astragalus membranaceus*)

Astragalus, a well-known tonic herb used for thousands of years in China, is a native to northern and eastern China and Mongolia. The key constituents of Astragalus include polysaccharide, triterpenoid saponins (Astrahalosides), flavonoids, choline, betaine, kumatakenin, sterols, linoleic acid and linolenic acid.

Motherwort (*Leonurus cardiaca*)

Indigenous to central Asia, it is now widely grown in most of Europe and North America. Chemical constituents in the aerial part of the plant, which is used therapeutically, include alkaloids (L-stachydrine, leonurine), diterpenoids (leocardin), bitter glycosides, triterpenes (ursolic acid), iridoid glucoside, flavonoids, caffeic acid and tannins. This herb is particularly useful at menopause to prevent tachycardia or to inhibit cardiac palpitations and stabilize blood vessel sensitivity to fluctuation estrogen levels as well as protecting against coronary heart disease.

EXAMPLES

Having generally described this invention, a further understanding can be obtained by reference to certain specific examples which are provided herein for purposes of illustration only and are not intended to be limiting unless otherwise specified.

A clinical study was undertaken comparing a phytoestrogen formula, Formula #1 in Table 1 below, with a formula of the present invention containing certain phytoestrogens and a mixture of other herbs for relief of menopausal symptoms. Each composition was given to 10 patients for a period of 14 days, and the patients monitored to gain their comments on general well-being, possible menopausal symptoms and side effects.

TABLE 1

| | Formula #1 | | Formula #2 | |
| --- | --- | --- | --- | --- |
| | mg/day | extract concentration | mg/day | extract concentration |
| Red Clover | 200 | 5:1 | — | — |

TABLE 1-continued

| | Formula #1 | | Formula #2 | |
| --- | --- | --- | --- | --- |
| | mg/day | extract concentration | mg/day | extract concentration |
| Soy isoflavones | 200 | n/a | 100 | n/a |
| Black Cohosh | 80 | 4:1 | 200 | 4:1 |
| Wild Yam | 100 | n/a | 66.7 | n/a |
| Sage | — | — | 50 | 4:1 |
| Vervain | — | — | 25 | 4:1 |
| Astragalus | — | — | 25 | 4:1 |
| Motherwort | — | — | 25 | 4:1 |
| Chastetree Berry | — | — | 25 | 4:1 | n/a = not available/unknown

The women using the formula of the present invention, Formula #2, reported all symptoms of insufficient estrogen production had disappeared, and a renewed sense of well-being, as well as decreased irritability.

Preliminary patient comments included:

"I noted a greater sense of well-being. I felt like my old self again."

"My friends noticed my attitude has improved and so they are taking the product, too."

"My hot flashes have completely gone away and I'm finally sleeping though the night again."

"I felt much better after the first month. After four months, the vaginal dryness went away and I don't have pain with intercourse anymore."

In contrast, patients taking Formula #1, containing only the phytoestrogens, including red clover, reported continued difficulties with menopausal symptoms such as hot flashes, insomnia and vaginal dryness, as well as increased incidence of complications such as fatigue, absentmindedness and lack of energy.

Surprisingly, removal of the red clover (long thought to be a highly effective phytoestrogen) and addition of various herbs used in treating the complications as well as menopausal type symptoms gave unexpected improvements in patient well-being and relief from the effects of reduced estrogen production.

Obviously, additional modifications and variations of the present invention are possible in light of the above teachings. It is therefore to be understood that within the scope of the appended claims, the invention may be practiced otherwise than as specifically described herein.

What is claimed is:

1. A method of treating symptoms associated with reduced estrogen production, comprising: administering to a subject in need thereof an effective amount of a composition comprising a) at least one phytoestrogen containing food, herb or an extract thereof and b) at least four herbs selected from the group consisting of sage, chastetree berry, vervain, astragalus, motherwort and extracts thereof.

2. A composition comprising:
   a) at least one phytoestrogen containing food, herb or an extract thereof, and
   b) at least four herbs selected from the group consisting of sage, chastetree berry, astragalus, motherwort, vervain and their extracts.

3. The method of claim 1 wherein said at least one phytoestrogen containing herb is at least one member selected from the group consisting of soy, wild yam, black cohosh and extracts thereof.

4. The method of claim 1, wherein said composition is in a form selected from the group consisting of capsule, soft gelatin capsule, tablet, caplet, powder and liquid.

5. The method of claim 1, wherein the composition comprises at least two phytoestrogen containing herbs or extracts thereof.

6. The method of claim 5, wherein the composition comprises at least three phytoestrogen containing herbs or extracts thereof.

7. The method of claim 3, wherein said composition comprises each of soy, wild yam, black cohosh or extracts thereof, and each of sage, vervain, chastetree berry, motherwort, astragalus or extracts thereof.

8. The method of claim 7, wherein the composition comprises from about 1 to about 500 mg soy isoflavones;

from about 1 to about 500 mg black cohosh;

from about 1 to about 500 mg wild yam;

from about 1 to about 500 mg sage;

from about 1 to about 500 mg chastetree berry;

from about 1 to about 500 mg vervain;

from about 1 to about 500 mg astragalus; and from about 1 to about 500 mg motherwort as the herb or its extract in an equivalent extract dosage.

9. The method of claim 1, wherein the composition is administered either as a single dose or as multiple doses per day.

10. The method of claim 1, wherein the composition is administered in an effective daily dosage of from 0.1 to 10,000 mg/day.

11. The method of claim 10, wherein the composition is administered in an effective daily dosage of from 30 to 800 mg/day.

12. The method of claim 9, wherein the composition is administered in multiple doses per day, wherein the doses are equal dosages.

13. The method of claim 9, wherein the composition is administered in multiple doses per day, wherein the doses are unequal dosages depending on time between doses, in order to maintain a more constant level of active ingredients in said subject.

14. The method of claim 1, wherein the composition further comprises one or more conventional pharmaceutical excipients or food ingredients.

15. The composition of claim 2, wherein said at least one phytoestrogen containing herb or its extract is at least one member selected from the group consisting of soy, wild yam, black cohosh and extracts thereof.

16. The composition of claim 2, wherein said composition is in a form selected from the group consisting of capsule, soft gelatin capsule, tablet, caplet, powder and liquid.

17. The composition of claim 2, wherein the composition comprises at least two phytoestrogen containing herbs or extracts thereof.

18. The composition of claim 17, wherein the composition comprises at least three phytoestrogen containing herbs or extracts thereof.

19. The composition of claim 15, wherein said composition comprises each of soy, wild yam, black cohosh or extracts thereof, and each of sage, vervain, chastetree berry, motherwort, astragalus or extracts thereof.

20. The composition of claim 19, wherein the composition comprises from about 1 to about 500 mg soy;

from about 1 to about 500 mg black cohosh;

from about 1 to about 500 mg wild yam;

from about 1 to about 500 mg sage;

from about 1 to about 500 mg chastetree berry;

from about 1 to about 500 mg vervain;

from about 1 to about 500 mg astragalus; and from about 1 to about 500 mg motherwort as the herb or its extract in an equivalent extract dosage.

* * * * *